United States Patent
Melton, Jr.

[19]

[11] Patent Number: 6,038,465
[45] Date of Patent: Mar. 14, 2000

[54] TELEMEDICINE PATIENT PLATFORM

[75] Inventor: Hewlett E. Melton, Jr., Sunnyvale, Calif.

[73] Assignee: Agilent Technologies, Inc., Palo Alto, Calif.

[21] Appl. No.: 09/170,542

[22] Filed: Oct. 13, 1998

[51] Int. Cl.[7] .............................. G07D 7/00; G06K 9/00; A61B 10/00; G06F 17/00; G01G 19/40
[52] U.S. Cl. .................. 600/407; 600/587; 177/25.19; 177/245; 340/825.34; 382/115; 128/920; 128/922; 73/597; 73/602; 181/126
[58] Field of Search ............................ 177/210 R, 245, 177/25.13, 25.19; 340/825.34; 33/700; 600/407, 587; 128/920, 922; 181/126; 382/115; 73/597, 602

[56] References Cited

U.S. PATENT DOCUMENTS

| Re. 29,008 | 10/1976 | Ott | 600/587 |
|---|---|---|---|
| 3,872,443 | 3/1975 | Ott | 600/587 |
| 3,990,436 | 11/1976 | Ott | 600/407 |
| 4,048,986 | 9/1977 | Ott | 600/407 |
| 4,107,775 | 8/1978 | Ott | 382/115 |
| 4,154,114 | 5/1979 | Katz et al. | 181/126 |
| 4,366,873 | 1/1983 | Levy et al. | 177/25.19 |
| 4,576,244 | 3/1986 | Zeigner et al. | 177/245 |
| 4,773,492 | 9/1988 | Ruzumna | 177/25.19 |
| 4,844,187 | 7/1989 | Jabero | 177/25.19 |
| 4,923,024 | 5/1990 | Ferrer et al. | 177/245 |
| 5,305,390 | 4/1994 | Frey et al. | 340/825.34 |
| 5,415,176 | 5/1995 | Sato et al. | 600/547 |
| 5,452,722 | 9/1995 | Langton | 128/660.06 |
| 5,800,350 | 9/1998 | Coppleson et al. | 600/547 |
| 5,871,446 | 2/1999 | Wilk | 600/407 |
| 5,878,746 | 3/1999 | Lemelson et al. | 128/920 |

*Primary Examiner*—Randy W. Gibson

[57] ABSTRACT

A system and a method for remote monitoring of a designated user utilize an integrated scale that is able to measure the body weight of a current user and determine whether the current user is the designated user. The identification of the current user is accomplished by measuring a preselected length of the current user by reflecting sound waves at location(s) that defines the preselected length and comparing the measured length to a corresponding length of the designated user that is stored in the integrated scale. When the current user is identified as the designated user, the integrated scale transmits the measured body weight to a remote monitoring device. The preselected length may be the distance from the bottom of a foot to the knee joint. Alternatively, the preselected length may be the length of a tibia or femur, or the skeletal height. The integrated scale may include devices to measure the heart rate and the respiratory rate of the current user by transmitting sounds waves and recording reflected sound waves from the chest cavity and the heart chambers.

20 Claims, 6 Drawing Sheets

TELEMEDICINE PATIENT PLATFORM

TECHNICAL FIELD

The invention relates generally to weight monitoring systems and more particularly to a remote weight monitoring system capable of automatically identifying a designated user.

DESCRIPTION OF THE RELATED ART

Weight scales are common household items used to monitor body weights of individuals. Monitoring body weight is important for many people, such as patients with congestive heart failure (CHF) or members of weight control programs.

In CHF patients, abnormal fluid accumulation is an indication for potential complications. An increase in the body weight of a CHF patient may be a result of abnormal fluid accumulation. Therefore, the body weights of CHF patients are regularly monitored to detect significant changes. With early detection of fluid accumulation and preventive treatment, acute episodes of congestive failure may be avoided, circumventing expensive hospitalization.

In most situations, patients report their current body weight to their health provider by telephone. A patient would weigh him/herself in a conventional manner at home using a common weight scale. The patient would then call the health provider to report his/her current weight. This process is repeated on a regular basis to monitor the patient's weight over time. In this simple procedure, most of the burden lies with the patients to measure and report their current body weight to their health providers.

Although coronary disease often begins at an early age, congestive heart failure is widely prevalent in elderly persons. Currently, about 8% of people above the age of 65 have CHF. For these elderly patients, the above-described procedure can be a burdensome task. In addition, this procedure introduces human errors in the reporting process.

Use of sophisticated scales with computer interfaces can alleviate human error. The scales may be directly linked to a computer of a health provider, such that the measured body weight can be transmitted from the scale to the health provider without being relayed by the patient. However, the patient would still be required to identify him/herself by inputting codes or other identifiers into the scale in order for the computer of the health provider to recognize that particular patient. Again, the procedure can be burdensome for elderly patients with CHF.

In a commercial weight control program environment, the support provided by program managers and peer groups is a vital part of an effective program. However, monitoring body weight is also an essential part of the program. The program may be tailored in accordance with the shift in body weight to meet the needs of individuals. For example, if the body weight of a particular member continues to rise after a certain time period, the focus of the program may divert from physical factors, such as eating habits and exercise, to psychological factors, such as issues in relationships.

Typically, members of weight control programs maintain a log of body weight in order to chart any changes in their body weight. The burden of manually inputting measured body weight into the log may discourage continued participation in the program. In addition, temptations to fudge the entries by members may lead to inaccurate evaluations of their progress. Again, scales with computer interfaces may alleviate inaccurate entries by the members of weight control programs. However, the user of the scale is burdened by the need to input codes or other identifiers to identify him/herself as the person on the scale, which may lead to members not reporting their current body weights.

What is needed is a remote weight monitoring system wherein a weight scale is integrated with an identification device that can identify the user on the weight scale and selectively transmit information regarding body weight of a particular user to a remote device for evaluation.

SUMMARY OF THE INVENTION

A system and a method for remote monitoring of a designated person utilize an integrated scale that is able to measure the body weight of a user and determine whether the user is the designated person. The identification of the user is accomplished by employing second wave energy to enable a measurement of a preselected body-related length of the user and comparing the measured length to a prior measurement of corresponding body-related length of the designated person. The integrated scale is able to measure the preselected length of the user by calculating the propagation time of sound waves reflected at one or more structures (e.g., bones or soft tissue within the user.)

The system includes the integrated scale and a remote monitoring device that are communicatively linked to exchange information. Preferably, the integrated scale is located at the residence of the designated person, while the remote monitoring device is located at a monitoring facility. The system may be utilized to monitor patients with congestive heart failure (CHF) or members of weight control programs from their homes or other locations. The integrated scale functions in a similar manner as conventional weight scales to measure the body weight of any person who steps onto a platform of the integrated scale. However, the integrated scale transmits the measured body weight of the user to the remote monitoring device only if the ultrasonically based measurement identifies the user as the designated person.

Initially, a reference value is stored into memory of the integrated scale. The reference value represents the prior measurement of the body-related length of the designated person that will be compared to a measurement of the current user on the integrated scale. When the current user steps onto the integrated scale, the integrated scale calculates the relevant body-related length of the current user in order to determine whether the current user is the designated person. As one example, the preselected length may be the distance from the bottom of a foot to the knee joint, the length D. Alternatively, the preselected length may be the length of a tibia or femur, or even the skeletal height.

The integrated scale utilizes sound waves to calculate the preselected length of the current user. An acoustic transducer is employed by the integrated scale to derive a measured value of, for example, the length D of the current user. The acoustic transducer emits sound waves into the user. When the sound wave impinges upon the knee joint, a portion of the sound wave energy is reflected by the knee joint. This reflected sound is received by the acoustic transducer. The measured value of the length D is derived by measuring the time for the sound wave energy to travel from the acoustic transducer to the knee joint and back. Using the speed of the sound wave through a known medium, i.e., bones, the measured value of the length D can be derived. The measured value is compared with the reference value to determine whether the current user is the designated person.

In one embodiment, the measured body weight of the current user is used in conjunction with the measured value of the body-related length to determine whether the current user is the designated person. The measured body weight of the current user is compared with a stored body weight of the designated person. If the measured body weight is within a prescribed range of the stored body weight, positive determination is made. Similarly, the measured length value is compared with the reference length value to determine whether the measured value is within a prescribed range of the reference value. Only when both the measured body weight and the measured length value fall within their respective ranges will the integrated scale establish communication with the remote monitoring device to transfer the measured body weight. The integrated scale operates to selectively transfer only the measured body weight of the designated person. When persons other than the designated person step onto the integrated scale, the integrated scale is able to distinguish those persons from the designated person, such that their measured body weights are not transferred to the remote monitoring device.

In other embodiments, the integrated scale is able to compare more than one preselected length. For example, the lengths of left tibia and femur may be incorporated in the identification process, such that these lengths are measured with respect to the current user and compared to stored reference values of the designated person to increase the accuracy of the identification. In addition, the skeletal height may be incorporated to further increase the accuracy.

The integrated scale may include devices to measure the heart rate and the respiratory rate of the current user. Using the same acoustic transducer or other transducers, time comparisons of sequential echoes from the chest cavity and the heart chambers may be utilized to measure the heart and respiratory rates. The measured rates can then be transmitted to the remote monitoring device only when the current user has been identified as the designated person. These measurements could provide health providers, or other monitoring personnel, a more complete picture of the current health of the designated person.

The invention provides an efficient means to monitor off-facility persons. Since only the information concerning the designated person is transferred to the remote monitoring device, the remote monitoring personnel is able to monitor the health of the designated person without the need to check whether the information received from the integrated scale is from the designated person or another person, such as a member of the household of the designated person or a visitor. In addition, the automatic identification feature of the integrated scale eliminates the need for the designated person to identify him/herself when using the integrated scale.

Furthermore, the invention may be configured to provide a variety of health-related information concerning the designated person in addition to the body weight, such as the heart rate, stroke volume, cardiac output, respiratory rate, tidal volume, body mass index, and postural changes.

DETAILED DESCRIPTION

Figure 1:
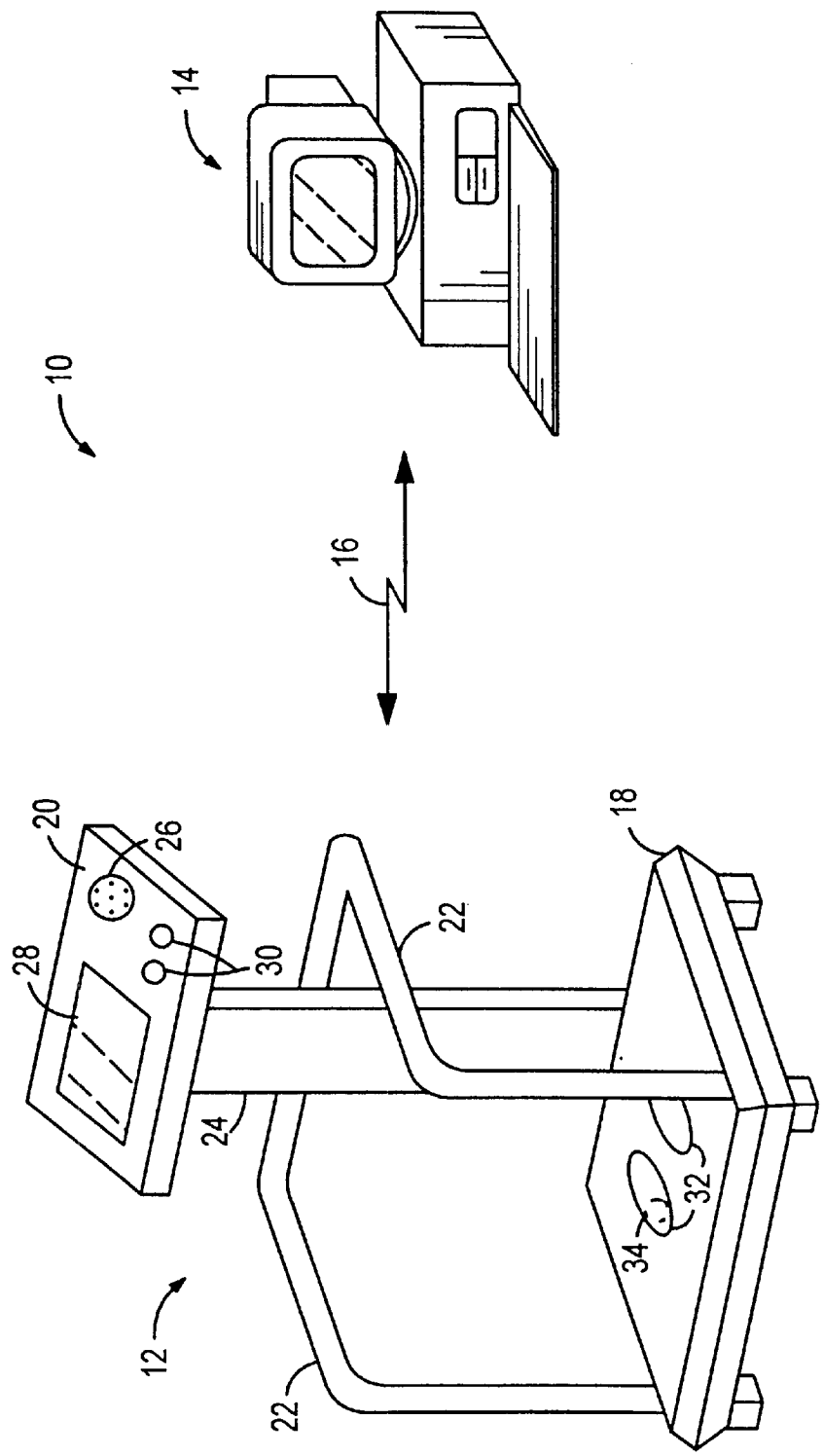
FIG. 1 is a perspective view of a weight monitoring system, showing an integrated scale and a remote monitoring device, in accordance with the invention.

With reference to FIG. 1, a weight monitoring system 10 is shown as including an integrated scale 12 and a remote monitoring device 14 that are communicatively connected by a communication link 16. The communication link 16 may be a telephony line or wireless connection. The weight monitoring system 10 facilitates automatic reporting of body weight and other health-related data of a particular person to a remote monitoring facility, where the remote monitoring device 14 is located. For example, the weight monitoring system 10 may provide remote monitoring of a patient with congestive heart failure by his/her health provider. Alternatively, the weight monitoring system 10 may provide remote monitoring of a member of a weight control program by a program manager. However, the invention will be described hereinafter with respect to patient and health provider environment.

In the preferred embodiment, the integrated scale 12 is located at the residence of the patient, while the remote monitoring device 14 is located at a hospital or other health care facility. The integrated scale 12 includes a platform 18, a control console unit 20, and a pair of handrails 22. The control console unit 20 is held in a position above the platform 18 by a frame 24. Both of the handrails 22 are attached to the platform 18 and the frame 24 to provide support for a user. The control console unit 20 is shown to contain a two-way speaker 26, a display monitor 28, and a number of control buttons 30. The two-way speaker 26 can provide verbal communication between the user of the integrated scale 12 and a health provider at the remote monitoring device 14. The display monitor 28 allows the user to view a variety of information concerning the status of the integrated scale 12. The display monitor 28 may also allow the user to view the health-related data being measured by the integrated scale 12. The platform 18 may include two foot markings 32. The foot markings 32 assist the user to properly position him/herself onto the platform 18.

The structure of the integrated scale 12 is not crucial to the invention. In addition, the control console unit 20, the frame 24 and the handrails 22 are not essential components of the integrated scale 12. In the most non-complex embodiment, the integrated scale 12 may only include the platform 18 with a simple display monitor (not shown).

The remote monitoring device 14 may be a conventional personal computer. The remote monitoring device 14 is configured to receive health-related data of a patient from the integrated scale 12. The health-related data is used by the health care personnel at the remote monitoring facility to diagnose the health of the patient. The remote monitoring device 14 is also able to receive information concerning the status of the integrated scale 12 in order to detect any malfunctioning of the scale. Although only a single integrated scale 12 is shown connected to the remote monitoring device 14 in FIG. 1, additional integrated scales may be associated with the remote monitoring device 14.

In operation, a user steps onto the platform 18 of the integrated scale 12. The user may utilize the handrails 22 to position him/herself on the platform 18, placing each foot on the foot marking 32. Preferably, the user is positioned in a standing position on the platform 18. The user then turns "on" the integrated scale 12 by activating one of the control buttons 30. Alternatively, the force exerted on the platform 18 by the user automatically turns "on" the integrated scale 12.

The integrated scale 12 measures the body weight of the user using conventional methods and devices within the platform 18 and displays the measured body weight on the display monitor 28 of the control console unit 20. In addition, the integrated scale 12 determines whether the measured body weight should be transmitted to the remote monitoring device 14. The integrated scale 12 is able to distinguish between different users, such that only when a designated user steps onto the integrated scale 12 communication is established between the integrated scale 12 and the remote monitoring device 14 to transfer the measured body weight information and any other health-related data. For example, the designated user may be a patient with congestive heart failure. When a user other than the designated user is on the integrated scale 12, the integrated scale 12 does not establish communication with the remote monitoring device 14. However, the integrated scale 12 may still operate to display the body weight and other health-related data on the display monitor 28 for viewing by the current user.

The integrated scale 12 is able to determine whether the current user is the designated user by initially measuring a preselected body-related length of that user. For example, the preselected length may be the distance from the bottom side of the left foot to the left knee joint of the user. The measured length is then compared with a stored value of the respective length of the designated user. If the measured length falls within a specified range of the stored value, the current user is identified as the designated user. However, if the measured length falls outside of the specified range, the integrated scale 12 determines that the current user is not the designated user.

The preselected length is measured by transmitting sound waves from an acoustic transducer 34, shown in phantom, located at the left foot marking 32 on the platform 18 in an upward direction. The integrated scale 12 can operate well utilizing a single acoustic transducer. However, the integrated scale 12 preferably contains two acoustic transducers, wherein the additional acoustic transducer is located at the right foot marking 32. The number of acoustic transducers is not critical to the invention. The sound waves then travel through the left foot and the left tibia. A portion of the sound wave energy is reflected when the left knee joint is impinged by the sound waves. The reflected sound wave energy then propagates back towards the platform 18, where it is detected by the same acoustic transducer 34.

The time interval between the emission of sound wave energy and reception of the reflected sound waves can be utilized to calculate the preselected length of the current user. Once the preselected length has been calculated, the measured length is compared with the stored value in order to determine whether the measured length falls within the specified range of the stored value. The result of the comparison is utilized to identify or negate the current user as the designated user. The operation of the integrated scale 12 with respect to the identification operation will be described in detail below with reference to FIGS. 2 and 3.

Since portions of the sound wave energy transmitted from the acoustic transducer will be reflected at various points along the propagation path through the user, the preselected length can be the length between any two of these reflecting points within the user. For example, the preselected length may be the length of a tibia or a femur. Alternatively, the preselected length can be the skeletal height of the user that is measured by utilizing the reflected sound from the top of the skull. The integrated scale 12 may be configured to measure more than one length to compare the current user to the designated user, in order to increase the accuracy of the identification procedure.

Figure 2:
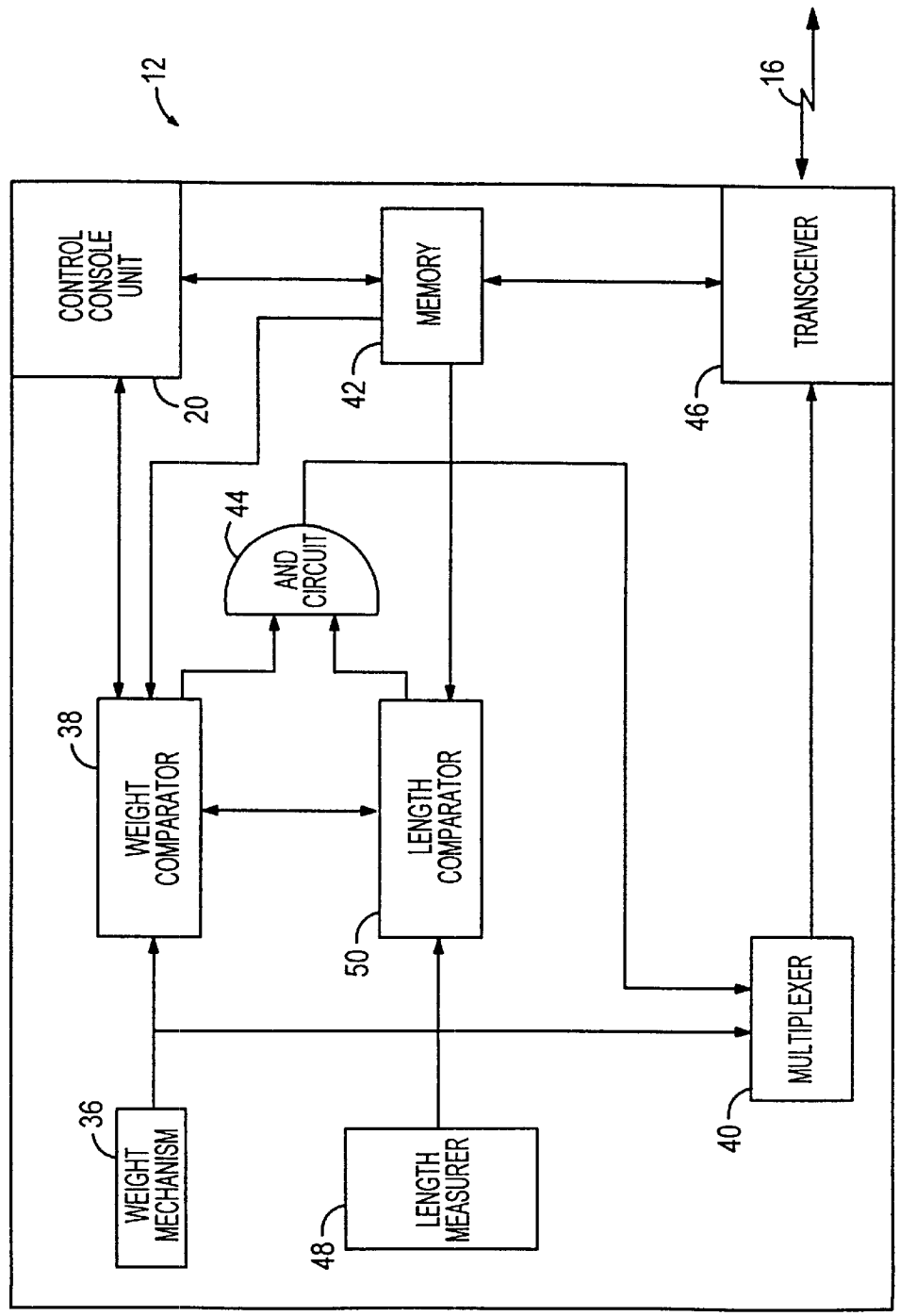
FIG. 2 is a block diagram of components of the integrated scale in accordance with one embodiment of the invention.

Turning to FIG. 2, a block diagram of components of the integrated scale 12 is shown. The integrated scale 12 shown in FIG. 2 is one of many potential embodiments of the integrated scale 12. In this embodiment, both the body weight and the preselected length of the current user are utilized for identification purposes. A weight mechanism 36 is connected to a weight comparator 38 and a multiplexer 40. The weight mechanism 36 can be a conventional device to measure the body weight of an individual. The weight comparator 38 is configured to compare the body weight measured by the weight mechanism 36 to a weight value stored in memory 42. Preferably, the weight value is the latest measured body weight of the designated user. If the measured weight falls within a prescribed range of the stored weight value, a confirmation signal is transmitted to an AND circuit 44. The multiplexer 40 is connected to a transceiver 46 to transmit body weight information to the remote monitoring device 14, shown in FIG. 1, if the current user is identified as the designated user.

The integrated scale 12 also includes a length measurer 48 that is coupled to a length comparator 50. The length measurer 48 contains the acoustic transducer 34, shown in FIG. 1, to measure the preselected length of the current user. The length measurer 48 and its operation will be described further below with reference to FIG. 3. Similar to the weight comparator 38, the length comparator 50 compares the measured length with a length value stored in the memory 42. The length value is the preselected length of the designated user. If the measured length falls within a prescribed range of the stored length value, a second confirmation signal is transmitted to the AND circuit 44. When the AND circuit 44 receives both confirmation signals from the weight and length comparators 38 and 50, the AND circuit 44 transmits a SEND signal to the multiplexer 40. The SEND signal directs the multiplexer to forward the measured body weight to the remote monitoring device 14 via the communication link 16.

On the other hand, if the AND circuit 44 receives a no confirmation signal from the comparators 38 and 50, or only one confirmation signal, the SEND signal is not transmitted to the multiplexer 40. In this situation, the current user has not been identified as the designated user. Therefore, the measured body weight is not transmitted to the remote monitoring device 14. However, the measured body weight may be relayed to the control console unit 20 for display.

Figure 3:
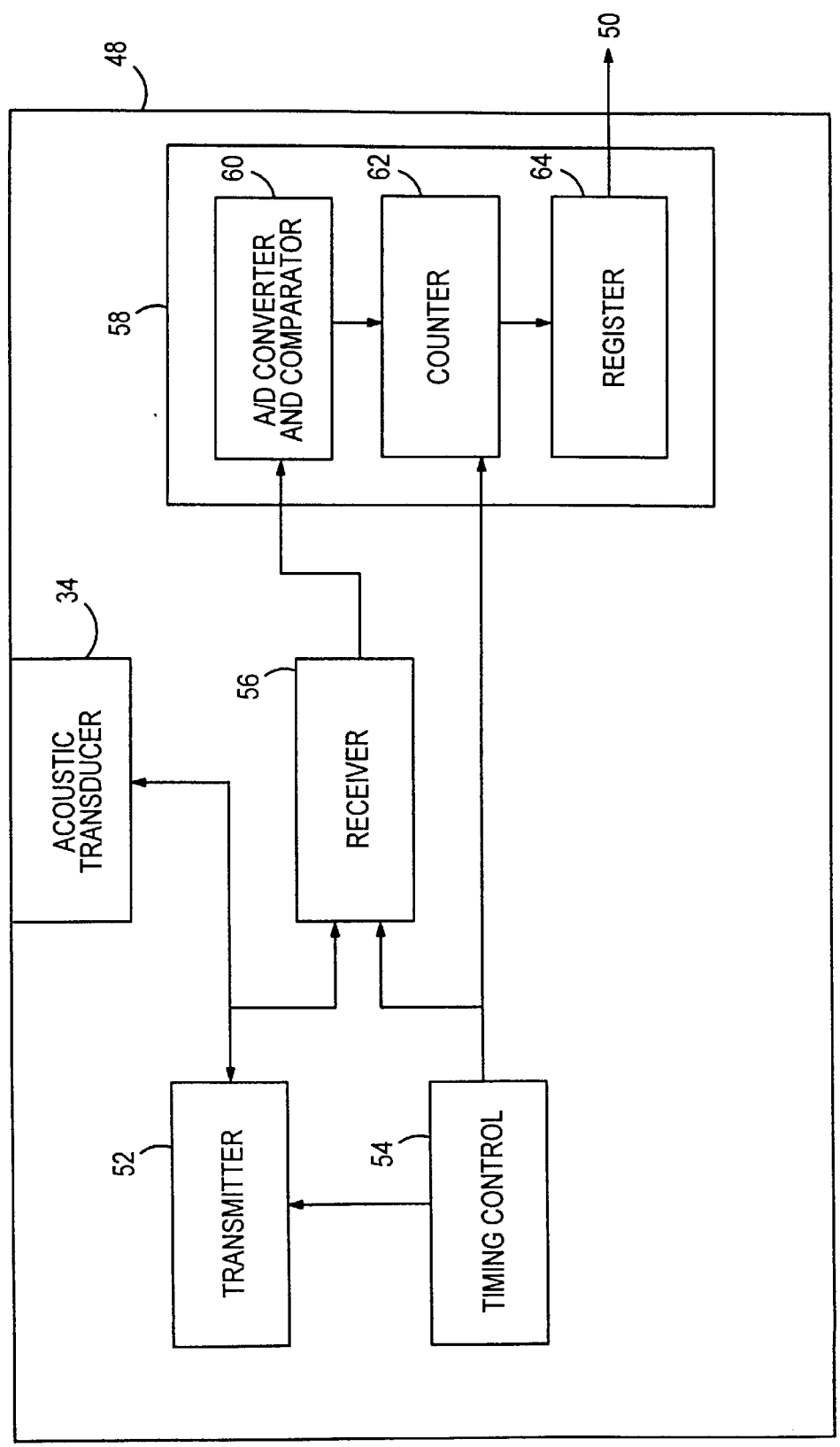
FIG. 3 is a block diagram of a length measuring component of the integrated scale of FIG. 2 in accordance with the invention.

In FIG. 3, components of the length measurer 48 are shown. The length measurer 48 includes the acoustic transducer 34, a transmitter 52, a timing control 54, a receiver 56 and a signal processor 58. The length measurer 48 can be configured to measure lengths by using either a pulse-echo sound method or a frequency domain method. In the pulse-echo sound method, a short pulse of sound energy is initially transmitted through a subject of interest from an acoustic transducer. Echoes of the pulse reflected from structures within the subject are received by the transducer. When an echo reflected from a desired structure within the subject of interest is received, the round trip time of the transmitted pulse is recorded. The round trip time and the propagation velocity of the pulse may be utilized to determine the distance of the structure from the transmission point. In the frequency domain method, continuous sound energy is transmitted and reflections caused by structures within the subject of interest are received, as the frequency of the sound waves is progressively increased or decreased. The reflections cause resonances and anti-resonances to occur. The frequency separation between the resonances and anti-resonances may be utilized to calculate distances between the structures. Although either method may be utilized, the length measurer 48 will be described as utilizing the pulse-echo method.

The signal processor 58 is shown in FIG. 3 as having an A/D converter and comparator 60, a counter 62 and a register 64. However, the signal processor 58 may include additional circuitry to perform more complex processing. The internal circuitry of the signal processor 58 of FIG. 3 is only an illustration of a compact configuration that can be employed to achieve basic functions of the signal processor 58.

Figure 5:
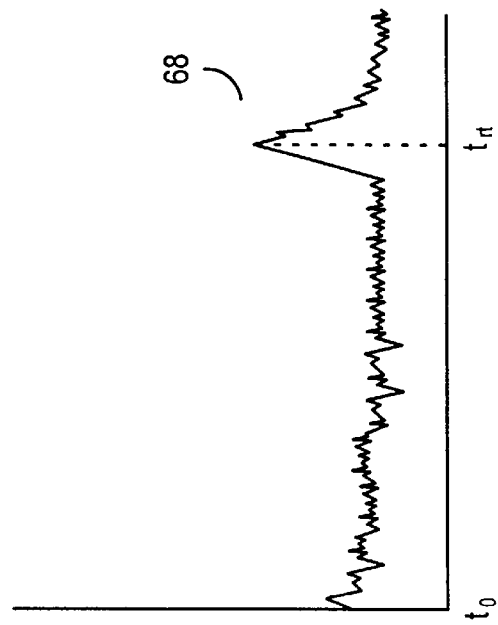
FIG. 5 is a graph illustrating an echo, reflected from a knee joint of the subject, received by the integrated scale.
Figure 4:
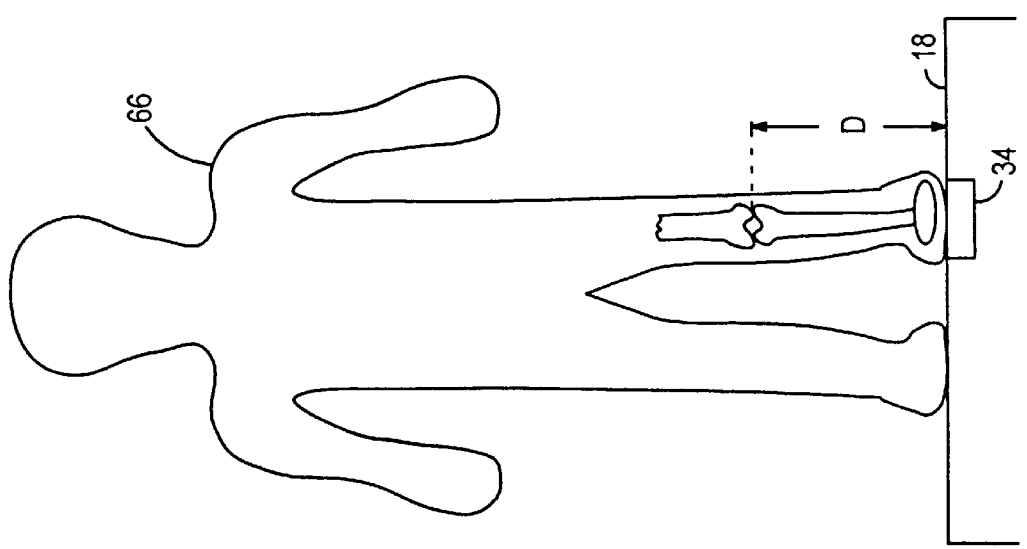
FIG. 4 is a view of a subject with partial illustration of the skeletal structure standing on the integrated scale.

The operation of the length measurer 48 will be described with reference to FIGS. 3, 4 and 5. In FIG. 4, a subject 66 is properly positioned on the platform 18 of the integrated scale 12 over the acoustic transducer 34. The preselected length of the subject 66 that will be measured by the length measurer 48 is D, the length from the acoustic transducer 34 to the knee joint of the subject 66. The length D is essentially the length from the bottom side of a foot to the knee joint. However, other lengths of the subject 66 may be utilized by the length measurer 48. By measuring the time for a sound pulse to travel from the acoustic transducer 34 to the knee joint and back, the length D can be calculated.

The length D measuring process begins at $t=t_0$, at which time a clock signal is sent from the timing control 54 to the transmitter 52, the receiver 56 and the counter 62. The clock signal directs the transmitter 52 to excite the acoustic transducer 34, which emits a pulse of sound wave energy in an upward direction towards the subject 66. Due to the frequency dependence of the acoustic energy attenuation, higher frequency sound waves are well suited to accurately measure structures in the lower portion of the subject 66, while lower frequency sound waves are able to provide better measurements for structures in the upper portion of the subject. Preferably, the acoustic transducer 34 generates sound waves having a frequency in the range of 100 to 200 kilohertz. However, the integrated scale 12 may utilize an acoustic transducer that generates sound waves having a frequency higher or lower than the preferred range, depending upon the desired measurements of a subject.

The pulse travels through the bottom left foot of the subject 66 and propagates towards the knee joint of the subject 66. Meanwhile, the counter 62 begins a digital count with the reception of the clock signal. By the time the pulse reaches the knee joint, the pulse has traveled the distance of D.

When the pulse impinges upon the knee joint, a portion of the pulse is reflected as an echo. The echo propagates back through the lower left leg of the subject 66 and is received by the acoustic transducer 34 at $t=t_{rt}$. The reflected echo is represented by a peak 68 in an electrical echo signal of FIG. 5. Peaks of other echoes caused by other structures before and after the knee joint within the subject 66 have been deleted from FIG. 5 for simplification. The electrical echo signal is transmitted from the acoustic transducer 34 to the receiver 56, where the echo signal is amplified. The amplified echo signal is then relayed to the A/D converter and comparator 60 of the signal processor 58. The A/D converter and comparator 60 determine whether the amplified echo signal is the desired signal. This can be performed by setting the A/D converter and comparator 60 such that only the echo signal from the knee joint will trigger the A/D converter and comparator 60 to produce an output signal. The output signal from the A/D converter and comparator 60 halts the counter 62, capturing the last count.

The capturing of the last count produces the data necessary to measure the round trip time as the product of the clock period and the count. By selecting a particular clock period, the captured count can represent the length D in a desired unit. For example, if the velocity of the sound wave energy through the lower leg of the subject 66 is taken to be approximately 3,000 meters per second, this velocity can be divided by two to represent the apparent velocity for the round trip. In other words, since the sound wave energy travels the distance twice the length D, the actual velocity can be divided by two to derive the value of length D. Therefore, the apparent velocity is approximately 1,500 meters per second or one centimeter for every 6.667 microseconds. By setting the clock period to 6.667 microseconds, every single count can represent one centimeter. To get a measurement in millimeters, the clock period can be set to 0.667 microseconds. Therefore, the captured count can represent the length D in either centimeters or millimeters, depending upon the clock period utilized. The measured length D is compared with a stored value for the same length of the designated user in the length comparator 50, shown in FIG. 2, in order to determine whether the subject 66 is the designated user. A positive determination of the length as well as the weight will direct the integrated scale 12 to transmit the measured body weight to the remote monitoring device 14 via the communication link 16.

With a more sophisticated signal processor, the integrated scale 12 may utilize the length of the left tibia as the preselected length for identification purposes. The length of the left tibia may be measured by first deriving the length D and subtracting the distance between the acoustic transducer 34 and the bottom of the tibia. In a similar manner, the length of the left femur may be utilized as the preselected length. The length of a femur may be derived by subtracting the length D from a distance between the acoustic transducer 34 and the hip joint. Alternatively, the skeletal height may be utilized as the identifier. The skeletal height may be approximated by the distance between the acoustic transducer 34 and the top of the skull of a subject. If a more accurate measurement is required, the soft tissue depth on the bottom of the feet can be subtracted out to fine tune the measurement.

The integrated scale 12 may be slightly modified to increase the accuracy of the identification process. The integrated scale 12 may be configured to calculate the lengths of a number of different bones and/or the skeletal height. The combination of these lengths can all be utilized to compare the subject with the designated user for a more accurate identification procedure.

Figure 6:
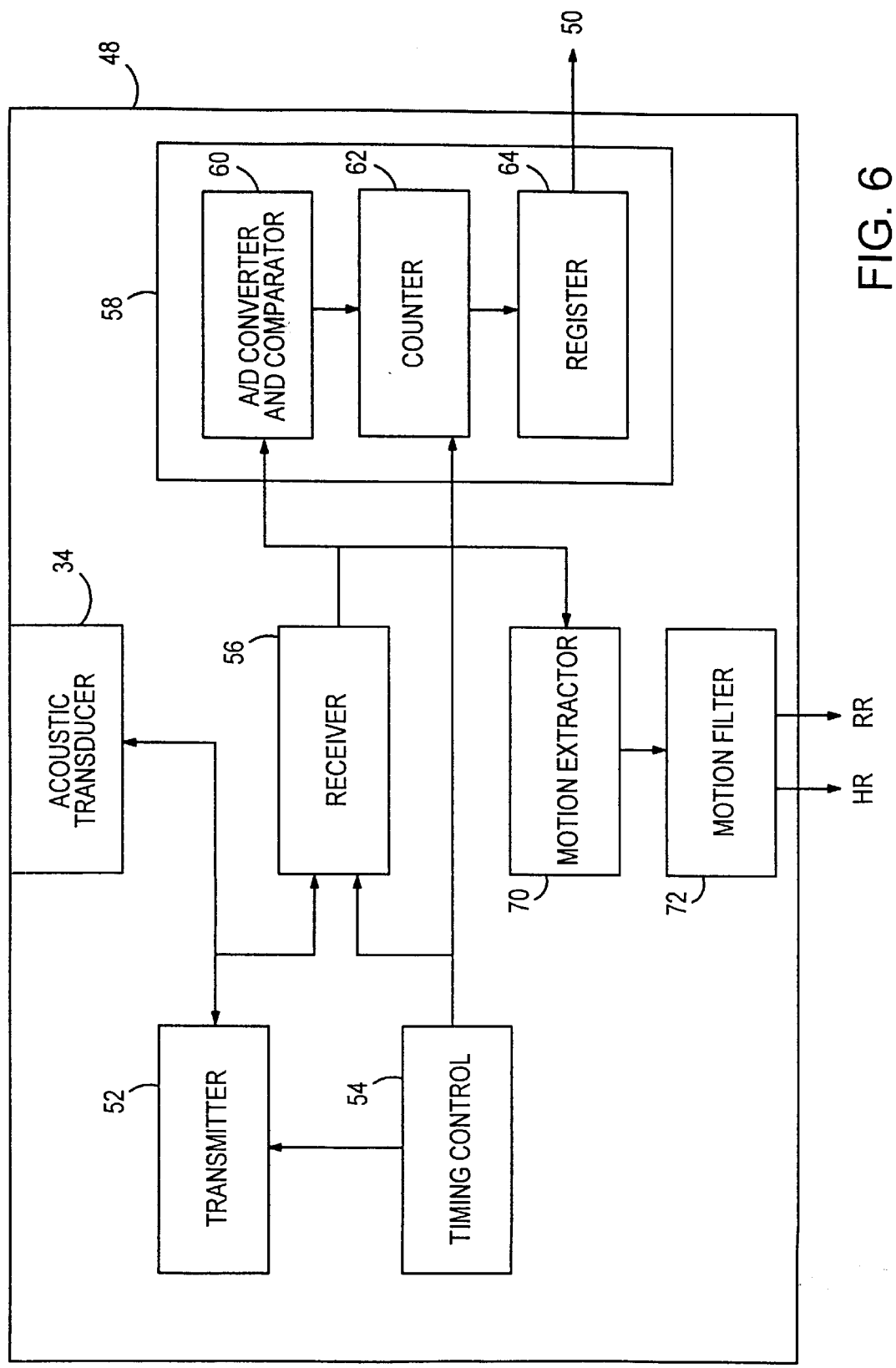
FIG. 6 is the length measuring component of FIG. 3 with additional devices to measure the heart and respiratory rate.

Turning to FIG. 6, another embodiment of the length measurer 48 is shown. In this embodiment, the length measurer 48 further includes a motion extractor 70 and a motion filter 72. The motion extractor 70 and the motion filter 72 operate to measure the heart rate (HR) and the respiratory rate of a subject on the integrated scale 12 by processing the acoustic echoes from the chest cavity and the heart chambers. These echoes can be used to extract motion of the lungs and the heart to derive the heart rate and the respiratory rate of the current user. The motion extractor 70 performs one of well known methods to extract motion caused by the heart and the lungs. For example, the motion extractor 70 may perform quadrature sampling for rate of phase change, doppler processing, or moving target indicator methods. The extracted motions are then separated by the motion filter 72 into heart rate and respiratory rate.

Alternative devices performing known methods may be employed to measure heart rate and respiratory rate. For example, the motion extractor 70 and the motion filter 72 may be replaced by a device to perform Fourier methods to directly extract the motion spectra with a peak occurring at the fundamental frequency for heart rate and another peak occurring at the fundamental frequency for respiratory rate. Alternatively, the device may perform wavelet techniques to extract the desired rates.

In a more sophisticated embodiment, the motion extractor 70 and the motion filter 72 may be replaced by a digital signal processor that can measure other heart and respiratory parameters, in addition to the heart and respiratory rates, from the acoustic echoes from the chest cavity and the heart chambers. For example, the digital signal processor may be configured to measure the heart stroke volume and the tidal volume of the lungs by determining the amplitudes in the echo-generated motion spectra relating to the heart and the lungs. Furthermore, the cardiac output of a subject may be determined by multiplying the measured heart rate with the measured stoke volume.

The measured heart and respiratory parameters are transmitted from the length measurer 48 to the control console unit 20 for display. In addition, the measured parameters are sent to the multiplexer 40. The measured parameters are then transmitted to the remote monitoring device 14, if the current user is identified as the designated user.

The integrated scale 12 may be further modified to meet the needs of patients, health providers, members of weight control programs, weight control program personnel, or other persons involved in remote health monitoring. For example, the integrated scale 12 may be slightly modified to measure and transmit skeletal height of the designated user. The skeletal height may be utilized by health providers to chart postural changes in the designated user.

By measuring the skeletal height and the body weight of the designated user, the body mass index of the designated user may also be calculated and transmitted to the health provider. Alternatively, the calculations may be performed at the remote monitoring device 14. Furthermore, the integrated scale 12 may be configured to monitor additional health-related signs, such as bowel activity and bladder volume of the designated user.

In addition, by using two acoustic transducers, the integrated scale may be able to remotely monitor the ability of the designated user to keep balance by measuring motion of two reference locations within the designated user. The integrated scale 12 may be employed to monitor other health-related signs where acoustic means can detect changes caused by the health-related signs.

Figure 7:
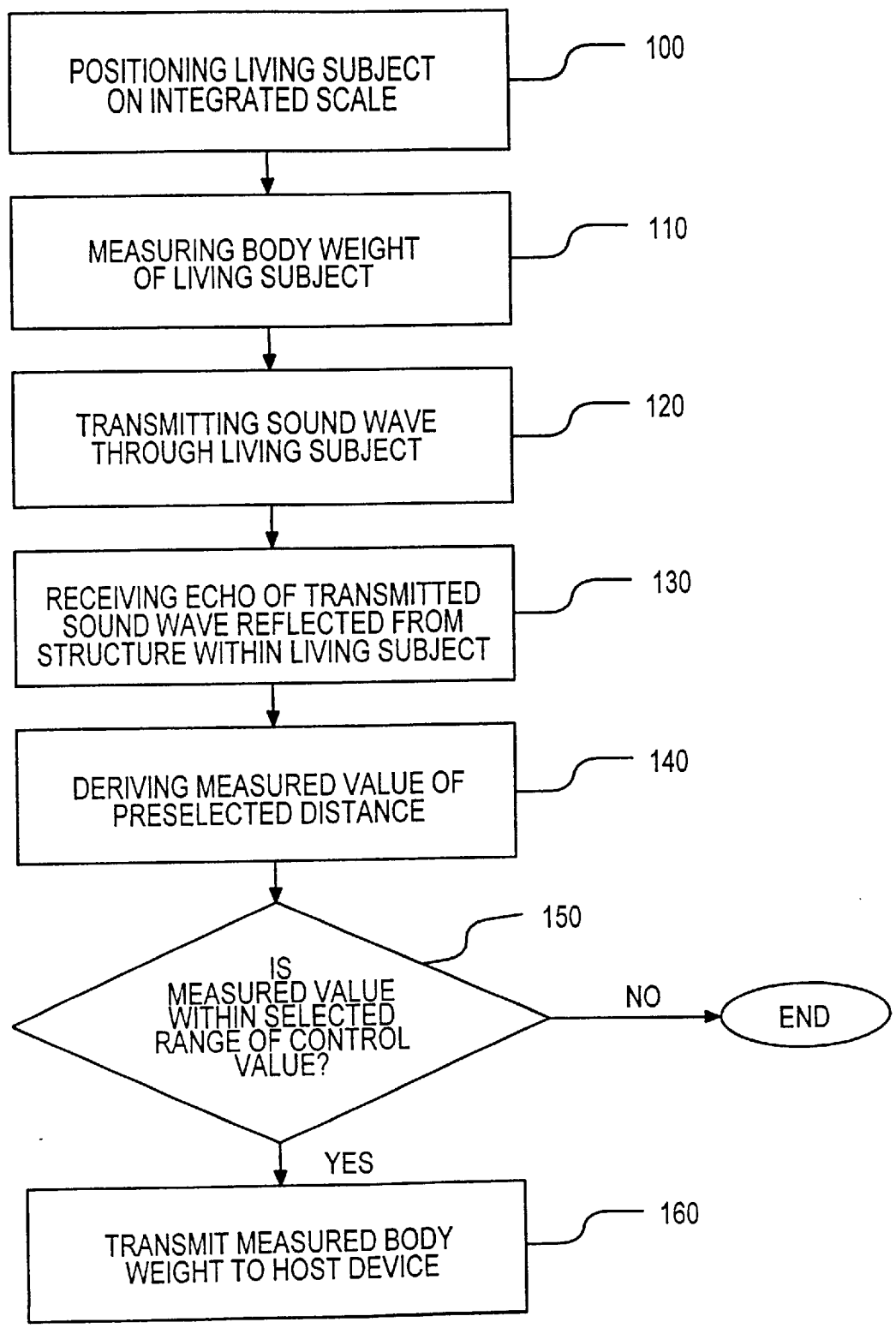
FIG. 7 is a flow diagram of a method of identifying a user utilizing the integrated scale in accordance with the invention.

A method of identifying a current user utilizing the integrated scale 12 in accordance with the invention will be described with reference to FIGS. 1 and 7. At step 100, the user is positioned on the integrated scale 12. Preferably, each foot of the user is placed on the foot marking 32. Following step 100, the body weight of the user may be measured by the integrated scale 12 at step 110. The body weight of the user is measured by utilizing conventional techniques. At step 120, a sound wave is transmitted from the acoustic transducer 34 to the user. The acoustic transducer 34 can be positioned such that the sound wave enters the left foot of the user and continues to propagate through the user. Next, at step 130, an echo of the transmitted sound wave is received by the acoustic transducer 34. The echo is a portion of the transmitted sound wave reflected from a structure within the user. For example, the echo may have been reflected from the left knee joint of the user.

At step 140, a measured value of a preselected distance is derived by measuring a time interval for the sound wave to traverse from a reference location to the structure and back. For example, if the preselected distance is the length of the left tibia, the time interval will include the duration in which the sound wave propagates from the bottom of the left tibia to the left knee joint and back to the bottom of the left tibia. Next, at step 150, the measured value is compared to a control value stored in the integrated scale 12. The control value is a corresponding distance of a known subject. Therefore, if the length of the left tibia is being utilized as the preselected distance, the control value will be the length of the left tibia of the known subject. If the measured value is not within a selected range of the control value, the process ends. However, if the measured value is within the selected range of the control value, the process continues to step 160. In step 160, the measured body weight is transmitted to the remote monitoring device 14 from the integrated scale 12. The heart and respiratory parameters of the user may be measured and transmitted to the remote monitoring device 14 at this time. Alternatively, measuring the heart and respiratory parameters may be performed prior to step 150 and then transmitted to the remote monitoring device 14, along with the measured body weight at step 160.

In another embodiment, the integrated scale 12 includes a second acoustic transducer, such that one transducer is configured to transmit sound waves while the other transducer is configured to receive the transmitted sound waves that have been reflected from a structure within the current user. For example, the acoustic transducer 34 of FIG. 1 may be configured to transmit a pulse of sound energy through the left leg of the current user. A portion of the pulse energy will be reflect when impinged upon the top of the skull of the current user. The reflected pulse energy is then received by the second transducer located beneath the right foot of the current user. In this manner, the skeletal height can be determined. Other preselected body-related lengths may be measured utilizing this embodiment.

Although the invention has been described above with respect to health monitoring systems, the invention could also function well in security systems. As an example, the integrated scale 12 of FIG. 1 may be modified to exclusively determine whether the current user is an authorized person allowed to enter a secured room or building. In this environment, the integrated scale is utilized to measure a unique physiological signature of the user. The physiological signature may be a skeletal signature, such as lengths of particular bones and/or the skeletal height. The measured physiological signature can be compared to stored signatures in a data bank to determine authorization for entry.

What is claimed is:

1. A system for identifying a subject of interest comprising:

sound transceiving means, having a surface adapted to interface with said subject of interest, for emitting sound waves into said subject of interest and receiving sound waves reflected from interfaces of structures within said subject of interest;

analyzing means operatively connected to said sound transceiving means for calculating a measured value representative of a distance between a first location and a second location by measuring a propagation time for said sound waves propagating through said subject of interest, at least one of said first and said second locations being an interface that induces back-reflection within said subject of interest; and evaluating means in communication with said analyzing means for comparing said measured value to a predetermined value calculated by measuring propagation time for sound waves propagating through a known subject.

2. The system of claim 1 further comprising a support platform to receive said subject of interest and a weighing means operatively connected to said platform for measuring a weight of said subject of interest by calculating a gravitational force exerted against said platform by said subject of interest.

3. The system of claim 1 wherein said subject of interest being identified is a living subject and wherein said sound transceiving means generates said sound waves at a frequency that induces back-reflection at interfaces of structures that include bones and soft tissues.

4. The system of claim 3 wherein said analyzing means is configured to measure a length of a tibia of said subject of interest, said first location and said second location defining extremities of said tibia.

5. The system of claim 3 wherein said analyzing means is configured to measure a length of a skeletal height of said subject of interest, said first location and said second location defining said skeletal height.

6. The system of claim 3 further comprising vital sign means for measuring a heart parameter and a respiratory parameter of said subject of interest, said vital sign means being coupled to said sound transceiving means to identify back-reflected sound wave energy that is indicative of positions of the heart and lungs of said subject of interest.

7. The system of claim 1 wherein said sound transceiving means is an acoustic transducer capable of producing said sound waves of a predetermined frequency, said acoustic transducer being configured to detect reflections of said sound waves.

8. The system of claim 7 wherein said acoustic transducer is configured to generate said sound waves having said predetermined frequency within a range of about 100 to 200 kilohertz.

9. The system of claim 7 wherein said acoustic transducer is positioned to emit said sound wave in a generally upward direction toward said subject of interest and receive said reflected said sound waves, which are propagating back from said subject of interest to said acoustic transducer.

10. The system of claim 1 further comprising an electrical transceiver electrically coupled to said evaluating means, said transceiver designed to establish communication with a host device in order to exchange information between said transceiver and said host device.

11. A system for identifying a living subject comprising:
an acoustic transducer designed to transmit sound waves and to receive an echo of said sound waves reflected from a preselected structure within said living subject;
a signal processor configured to calculate a measured value representing a distance from a reference location to said preselected structure, as a function of a measure of time sound wave energy propagating between said reference location and said preselected structure;
memory operatively associated with said signal processor having a capacity to store a control value representing a corresponding measure of distance with respect to a known subject; and a comparator coupled to said signal processor to receive and compare said measured value to said control value to determine whether said living subject is equivalent to said known subject.

12. The system of claim 11 further comprising a weight measuring mechanism operatively connected to said signal processor, said weight measuring mechanism including a support to receive said living subject, said weight measuring mechanism being configured to measure a body weight of said living subject.

13. The system of claim 11 wherein said acoustic transducer is configured to generate said sound wave having a frequency in a range of about 100 to 200 kilohertz.

14. The system of claim 11 wherein said signal processor is designed to determine a length of a tibia of said living subject, said length of said tibia being said distance from said reference location to said preselected structure, said reference location being at a first end of said tibia and said preselected structure being at a second end.

15. The system of claim 11 wherein said signal processor includes circuitry capable of determining a heart rate and a respiratory rate of said subject of interest utilizing a time comparison of a plurality of sound waves and associated echoes, emitted and received by said acoustic transducer.

16. A method of identifying a living subject of interest on a device comprising steps of:
positioning said living subject of interest on said device in a predetermined position;
transmitting a sound wave to said living subject of interest from said device such that said sound wave propagates through said living subject of interest;
receiving an echo of said sound wave caused by reflection of said sound wave at a structure within said living subject of interest;
determining a measured value of a preselected distance from said structure to a reference location by measuring a time interval for said sound wave to traverse from said reference location to said structure and said echo to re-traverse from said structure back to said reference location; and
comparing said measured value with a control value of a corresponding measure of distance of a known subject to determine whether said living subject of interest is said known subject.

17. The method of claim 16 further comprising a step of measuring a body weight of said living subject of interest while said living subject of interest is positioned on said device.

18. The method of claim 17 further comprising a step of selectively transmitting said body weight to a host device when a positive determination has been made that said living subject of interest is said known subject.

19. The method of claim 16 wherein said step of determining said measured value of said preselected distance includes calculating a length of a tibia of said living subject of interest, said length of said tibia defining said preselected distance.

20. The method of claim 16 further comprising a step of measuring a heart parameter and a respiratory parameter of said living subject of interest and a step of selectively transmitting information regarding said heart parameter and said respiratory parameter to a host device when a positive determination has been made that said living subject of interest is said known subject.

* * * * *